United States Patent
Stamires et al.

(12) 
(10) Patent No.: US 6,468,488 B1
(45) Date of Patent: Oct. 22, 2002

(54) MG-AL ANIONIC CLAY HAVING 3R$_2$ STACKING

(75) Inventors: Dennis Stamires, Newport Beach, CA (US); Paul O'Connor, Hoevelaken (NL); William Jones, Cambridge (GB)

(73) Assignee: Akzo Nobel N.V., Arnhem (NL)

( * ) Notice: Subject to any disclaimer, the term of this patent is extended or adjusted under 35 U.S.C. 154(b) by 134 days.

(21) Appl. No.: 09/636,693

(22) Filed: Aug. 11, 2000

Related U.S. Application Data

(63) Continuation-in-part of application No. 09/372,554, filed on Aug. 11, 1999, now abandoned.

(51) Int. Cl.$^7$ .............................. B01J 21/04; B01J 21/10
(52) U.S. Cl. .............................. 423/239.1; 423/244.01; 423/244.09; 423/593; 423/600; 423/625; 423/635; 502/80; 502/84; 502/414; 252/363.5; 252/397
(58) Field of Search .............................. 502/80, 84, 414; 423/593, 600, 625, 635, 239.01, 244.01, 244.09; 252/363.5, 397

(56) References Cited

U.S. PATENT DOCUMENTS

| | | | |
|---|---|---|---|
| 3,796,792 A | 3/1974 | Miyata et al. | 423/250 |
| 3,879,523 A | 4/1975 | Miyata et al. | 423/250 |
| 3,879,525 A | 4/1975 | Miyata et al. | 423/277 |
| 4,351,814 A | 9/1982 | Miyata et al. | 423/306 |
| 4,458,026 A | 7/1984 | Reichle | 502/80 |
| 4,656,156 A | 4/1987 | Misra | 502/415 |
| 4,843,168 A * | 6/1989 | Drezdzon et al. | 558/357 |
| 4,904,457 A | 2/1990 | Misra | 423/115 |
| 4,946,581 A | 8/1990 | van Broekhoven | 208/120 |
| 4,952,382 A | 8/1990 | van Broekhoven | 423/244 |
| 5,114,898 A | 5/1992 | Pinnavaia et al. | 502/406 |
| 5,399,537 A | 3/1995 | Bhattacharyya et al. | 502/84 |
| 5,439,861 A | 8/1995 | Bhattacharyya et al. | 502/84 |
| 5,507,980 A | 4/1996 | Kelkar et al. | 264/15 |
| 5,578,286 A | 11/1996 | Martin et al. | 423/593 |
| 5,591,418 A | 1/1997 | Bhattacharyya et al. | 423/239.1 |
| 6,171,991 B1 * | 1/2001 | Stamires et al. | 501/108 |
| 6,333,290 B1 * | 12/2001 | Stamires et al. | 501/125 |

FOREIGN PATENT DOCUMENTS

| | | | |
|---|---|---|---|
| EP | 0 536 879 | 4/1993 | C01G/1/00 |
| WO | WO/91/10505 | 7/1991 | B01J/8/00 |

OTHER PUBLICATIONS

*Materials Chemistry and Physics*, Textural Properties of Hydrotalcite–Like Compounds . . . 14, pp. 569–579 (1986).
*Clays and Clay Minerals*, Syntheses of Disordred and Al–Rich Hydrotalcite–Like Compounds 34, pp. 507–510, vol. 34, No. 5, (1986).
*Clays and Clay Minerals*, Physico–Chemical Properties of Synthetic Hydrotalcites in Relation to Composition, vol. 28, No. 1, pp. 50–56, (1980).
*Clays and Clay Minerals*, The Syntheses of Hydrotalite–Like Compounds and Their Structures and Physico–Chemical . . . ., vol. 23, pp. 369–375, (1975).
*J. Am. Ceram. Soc.*, Studies on $4CaO-Al_2O_3-13H_2O$ and the Related Natural Mineral Hydrocalumite 42, No. 3, pp. 121–126, (1959).
*Chemistry Letters*, Synthesis of New Hydrotalcit–Like Compounding and Their Physico–Chemical Properties, pp. 843–848, (1973).
*Anionic Clays: Trends in Pillary Chemistry*, Synthesis of Microproous Materials (1992), 2, pp. 108–165.
*Catalysis Today*, Hydrotalcite–Type Anionic Clays: Preparation, Properties and Applications 11, pp. 173–301, (1991).
*Clays and Clay Minerals*, Polytype Diversity of The Hydrotalcite–Like Minerals II. Determination of the Polytypes of Experimentally Studied Varieties, vol. 41, No. 5, 558–564, 1993.
*Clays and Clay Minerals*, Polytype Diversity of the Hydrotalcite–Like Minerals I. Possible Polytypes and their Diffraction Features, vol. 41, No. 5, 551–557, 1993.
*Hel. Chim. Acta*, 25pp. 106–137 and 555–569 (1942).

* cited by examiner

*Primary Examiner*—Stanley S. Silverman
*Assistant Examiner*—Christina Ildebrando
(74) *Attorney, Agent, or Firm*—Louis A. Morris

(57) ABSTRACT

The present invention pertains to Mg—Al anionic clay having 3R$_2$ stacking. This new polytype of anionic clay has a three-layer repeat, but it has a different interlayer arrangement than the conventional 3R$_1$ hydrotalcite. Said new polytype can be applied in all applications described before for the conventional 3R$_1$ polytype anionic clay such as in catalyst compositions, catalyst additive compositions, catalyst supports, absorbent compositions, stabilizer compositions and in medicaments.

25 Claims, No Drawings

MG-AL ANIONIC CLAY HAVING 3R$_2$ STACKING

REFERENCE TO RELATED APPLICATION

This application is a continuation-in-part of U.S. application Ser. No. 09/372,554, filed Aug. 11, 1999 now abandoned.

BACKGROUND OF THE INVENTION

1. Field of the Invention

This invention pertains to a new polytype of Mg—Al anionic clay.

2. Description of the Prior Art

Anionic clays have a crystal structure which consists of positively charged layers built up of specific combinations of metal hydroxides between which there are anions and water molecules. Hydrotalcite is an example of a naturally occurring anionic clay, in which carbonate is the predominant anion present. Meixnerite is an anionic clay wherein OH$^-$ is the predominant anion present.

In hydrotalcite-like anionic clays the brucite-like main layers are built up of octahedra alternating with interlayers in which water molecules and anions, more particularly carbonate ions, are distributed. The interlayers contain anions such as NO$_3^-$, OH$^-$, Cl$^-$, Br$^-$, I$^-$, SO$_4^{2-}$, SiO$_3^{2-}$, CrO$_4^{2-}$, BO$_3^{2-}$, MnO$_4^-$, HGaO$_3^{2-}$, HVO$_4^{2-}$, ClO$_4^-$, BO$_3^{2-}$, pillaring anions such as V$_{10}$O$_{28}^{-6}$ and MO$_7$O$_{24}^{6-}$, mono-carboxylates such as acetate, dicarboxylates such as oxalate, and alkyl sulfonates such as laurylsulfonate.

Anionic clays have a layered structure corresponding to the general formula

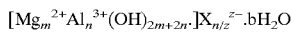
$$[Mg_m^{2+}Al_n^{3+}(OH)_{2m+2n}].X_{n/z}^{z-}.bH_2O$$

Wherein m and n have a value such that m/n=1 to 10, preferably 1 to 6, and b has a value in the range of from 0 to 10, generally a value of 2 to 6 and often a value of about 4. X may be CO$_3^{2-}$, OH$^-$ or any other anion normally present in the interlayers of anionic clays. It is more preferred that m/n should have a value of 2 to 4, more particularly a value close to 3.

It should be noted that a variety of terms is used to describe the material which is referred to in this patent as an anionic clay. Hydrotalcite-like and layered double hydroxide are interchangeably used by those skilled in the art. In this patent application we refer to the materials as anionic clays, comprising within that term hydrotalcite-like and layered double hydroxide materials.

The preparation of anionic clays has been described in many prior art publications.

Two major reviews of anionic clay chemistry were published in which the synthesis methods available for anionic clay synthesis have been summarized, F. Cavani et al "Hydrotalcite-type anionic clays: Preparation, Properties and Applications," *Catalysis Today*", 11 (1991) Elsevier Science Publishers B. V. Amsterdam. J P Besse and others "*Anionic clays: trends in pillaring chemistry, its synthesis and microporous solids*" (1992), 2, 108, editors: M. I. Occelli, H. E. Robson, Van Nostrand Reinhold, N.Y.

In these reviews two structurally different forms of anionic clays are described: the 3R$_1$ (three-layer repeat) and the 2H$_1$ (two-layer repeat) corresponding to hydrotalcite and manasseite, respectively. The Mg—Al anionic clays prepared by conventional preparation methods such as co-precipitation, optionally followed by hydrothermal treatment or aging to increase the crystallite size, have a 3R$_1$ stacking. Also naturally occurring hydrotalcite has the 3R$_1$ stacking.

In the publications in *Clay and Clay Minerals*, Vol 41, No.5, pages 551–557 and pages 558–564 of Bookin and Drits, it is stated that 3R$_2$ polytypes have been observed in nature, however, only in sulfate Mg—Al anionic clays.

For further work on anionic clays, reference is given to the following articles:

*Helv. Chim. Acta*, 25, 106–137 and 555–569 (1942)
*J. Am. Ceram. Soc.*, 42, no. 3, 121 (1959)
*Chemistry Letters* (Japan), 843 (1973)
*Clays and Clay Minerals*, 23, 369 (197)
*Clays and Clay Minerals*, 28, 50 (1980)
*Clays and Clay Minerals*, 34, 507 (1996)
*Materials Chemistry and Physics*, 14, 569 (1986).

In addition there is an extensive amount of patent literature on the use of anionic clays and processes for their preparation.

The prior art described below describes the preparation of anionic clays by the co-precipitation method:

European Patent Application 0 536 879 describes a method for introducing pH-dependent anions into the clay. The clay is prepared by the addition of a solution of Al(NO$_3$)$_3$ and Mg(NO$_3$)$_2$ to a basic solution containing borate anions. The product is then filtered, washed repeatedly with water, and dried overnight. Additionally mixtures of Zn/Mg are used.

In U.S. Pat. No. 3,796,792 by Miyata et al. entitled "Composite Metal Hydroxides" a range of materials is prepared into which an extensive range of cations is incorporated, including Sc, La, Th, In, etc. In the examples given solutions of the divalent and trivalent cations are prepared and mixed with base to cause co-precipitation. The resulting products are filtered, washed with water, and dried at 80° C. Example 1 refers to Mg and Sb and Example 3 to Mg and Bi. Other examples are given, and in each case soluble salts are used to make solutions prior to precipitation of the anionic clay at high pH.

In U.S. Pat. No. 3,879,523 by Miyata entitled "Composite Metal Hydroxides" also a large number of preparation examples are outlined. The underlying chemistry, however, is again based on the co-precipitation of soluble salts followed by washing and drying. It is important to emphasize that washing is a necessary part of such preparations, because to create a basic environment for co-precipitation of the metal ions a basic solution is needed and this is provided by NaOH/Na$_2$CO$_3$ solutions. Residual sodium, for example, can have a significant deleterious effect on the subsequent performance of the product as a catalyst or oxide support.

In U.S. Pat. No. 3,879,525 (Miyata) very similar procedures are again described.

In U.S. Pat. No. 4,351,814 to Miyata et al. a method for making fibrous hydrotalcites is described. Such materials differ in structure from the normal plate-like morphology. The synthesis again involves soluble salts. For example, an aqueous solution of a mixture of MgCl$_2$ and CaCl$_2$ is prepared and suitably aged. From this a needle-like product Mg$_2$(OH)$_3$Cl.4H$_2$O precipitates. A separate solution of sodium aluminate is then reacted in an autoclave with the solid Mg$_2$(OH)$_3$Cl.4H$_2$O and the product is again filtered, washed with water, and dried.

In U.S. Pat. No. 4,458,026 to Reichle, in which heat-treated anionic clays are described as catalysts for aldol condensation reactions, again use is made of magnesium and aluminum nitrate salt solutions. Such solutions being added to a second solution of NaOH and Na$_2$CO$_3$. After precipitation the slurry is filtered and washed twice with distilled water before drying at 125° C.

In U.S. Pat. No. 4,656,156 to Misra the preparation of a novel absorbent based on mixing activated alumina and hydrotalcite is described. The hydrotalcite is made by reacting activated MgO (prepared by activating a magnesium compound such as magnesium carbonate or magnesium hydroxide) with aqueous solutions containing aluminate, carbonate and hydroxyl ions. As an example the solution is made from NaOH, $Na_2CO_3$ and $Al_2O_3$. In particular, the synthesis involves the use of industrial Bayer liquor as the source of Al. The resulting products are washed and filtered before drying at 105° C.

In U.S. Pat. No. 4,904,457 to Misra a method is described for producing hydrotalcites in high yield by reacting activated magnesia with an aqueous solution containing aluminate, carbonate, and hydroxyl ions.

The methodology is repeated in U.S. Pat. No. 4,656,156.

In U.S. Pat. No. 5,507,980 to Kelkar et at al. a process is described for making novel catalysts, catalyst supports, and absorbers comprising synthetic hydrotalcite-like binders. The synthesis of the typical sheet hydrotalcite involves reacting pseudo-boehmite to which acetic acid has been added to peptize the pseudo-boehmite. This is then mixed with magnesia.

In U.S. Pat. No. 6,539,861 a process is disclosed for preparing a catalysts for synthesis gas production based on hydrotalcites. The method of preparation is again based, on the co-precipitation of soluble salts by mixing with base, for example, by the addition of a solution of $RhCl_3$, $Mg(NO_3)_2$ and $Al(NO_3)_3$ to a solution of $Na_2CO_3$ and NaOH.

Also in U.S. Pat. No. 5,399,537 to Bhattacharyya in the preparation of nickel-containing catalysts based on hydrotalcite use is made of the co-precipitation of soluble magnesium and aluminum salts.

In U.S. Pat. No. 5,591,418 to Bhattacharyya a catalyst for removing sulfur oxides or nitrogen oxides from a gaseous mixture is made by calcining an anionic clay, said anionic clay having been prepared by co-precipitation of a solution of $Mg(NO_3)_2$, $Al(NO_3)_3$ and $Ce(NO_3)_3$. The product again is filtered and repeatedly washed with de-ionized water.

In U.S. Pat. Nos. 4,946,581 and 4,952,382 to van Broekhoven co-precipitation of soluble salts such as $Mg(NO_3)_2$ and $Al(NO_3)_3$ with, and without the incorporation of rare earth salts was used for the preparation of anionic clays as catalyst components and additives. A variety of anions and di- and tri-valent cations are described.

In U.S. Pat. No. 5,114,898/WO 9110505 Pinnavaia et al. describe layered double hydroxide sorbents for the removal of sulfur oxide(s) from flue gases, which layered double hydroxide is prepared by reacting a solution of Al and Mg nitrates or chlorides with a solution of NAOH and $Na_2CO_3$. In U.S. Pat. No. 5,079,203/WO 9118670 layered double hydroxides intercalated with polyoxo anions are described, with the parent clay being made by co-precipitation techniques.

In U.S. Pat. No. 5,578,286 in the name of Alcoa a process for the preparation of meixnerite is described. Said meixnerite may be contacted with a dicarboxylate or polycarboxylate anion to form a hydrotalcite-like material.

As indicated in the description of the prior art given-above, there are many applications of anionic clays. These include but are not restricted to: catalysts, adsorbents, drilling muds, catalyst supports and carriers, extenders and applications in the medical field. In particular van Broekhoven has described their use in SOX abatement chemistry.

The present invention provides a new polytype of Mg—Al anionic clay. Said new polytype can be applied in all applications described herein before for the conventional $3R_1$ polytype anionic clay.

SUMMARY OF THE INVENTION

The present invention pertains to Mg—Al anionic clay having $3R_2$ stacking.

In a second embodiment, the invention comprises a process for the preparation of an Mg—Al anionic clay having $3R_2$ stacking wherein a slurry containing an aluminum source and a magnesium source is hydrothermally treated to form a Mg—Al anionic clay having $3R_2$ stacking.

In a third embodiment, the invention comprises a process for the preparation of Mg—Al anionic clay having $3R_2$ stacking wherein an anionic clay having $3R_1$ stacking is calcined, rehydrated and thermally treated to form Mg—Al anionic clay with $3R_2$ stacking.

In a fourth embodiment, the invention comprises shaped bodies containing Mg—Al anionic clay having $3R_2$ stacking.

In a fifth embodiment, the invention comprises a catalyst composition comprising Mg—Al anionic clay having $3R_2$ stacking.

In a sixth embodiment, the invention comprises a catalyst additive composition comprising Mg—Al anionic clay having $3R_2$ stacking.

In a seventh embodiment, the invention comprises a catalyst support comprising Mg—Al anionic clay having $3R_2$ stacking.

In an eighth embodiment, the invention comprises an absorbent composition comprising Mg—Al anionic clay having $3R_2$ stacking.

In a ninth embodiment, the invention comprises a stabilizer composition comprising Mg—Al anionic clay having $3R_2$ stacking.

In a tenth embodiment, the present invention comprises an Mg—Al-anionic clay having $3R_2$ stacking for use as a medicament.

Other objectives and embodiments of our invention encompass details about compositions, manufacturing steps, various uses of the anionic clay of the invention, etc., all of which are hereinafter disclosed in the following discussion of each of the facets of the present invention.

DETAILED DESCRIPTION OF THE INVENTION

This new polytype of anionic clay also has a three-layer repeat, but it has a different interlayer arrangement than the conventional $3R_1$ hydrotalcite. The two polytypes can be distinguished from each other by the intensities of the 107 and 108 reflections. The $3R_2$ type anionic clay has a stronger 107 reflection close to 45° 2 theta (as predicted by Drits and Bookin), whereas the $3R_1$ type has a stronger reflection close to 47° 2 theta (the 018 reflection). The presence of both a peak at 45 and 47° 2 theta of comparable intensities suggests the presence of a mixture of the two. It is understood that the precise 2 theta values for the 107 and 018 reflections will depend on the lattice a and c parameters for the Mg—Al anionic clay. Of course there are more differences in the X-ray diffraction pattern, but this is the best range of reflection to make a distinction because hardly any other reflections exist in that range from other compounds which are likely to be present as well in anionic clay-like material. For example, boehmite has a weak reflection in that range, but its presence can be excluded in the absence of a strong reflection between 13 and 15° 2 theta. Further, the new polytype Mg—Al anionic clay appears to have a different morphology from the conventional $3R_1$ type anionic clay, as can be seen by SEM examination. The $3R_2$ type anionic clay appears to have a structure with a irregular flake-like platelets which are randomly agglomerated. Conventional $3R_1$ anionic clay has regular well-formed layers of platelets that are arranged in the. usual bookstack form.

The new polytype anionic clay also has interlayers in which molecules of water and anions are distributed. The main anion will be hydroxide, but in addition to that other anions may be present in the new polytype anionic clay such as $NO_3^-$, $OH$, $Cl^-$, $Br^-$, $I^-$, $CO_3^{2-}$, bicarbonate, $SiO_3^{2-}$, $SO_4^{2-}$, $CrO_4^{2-}$, $BO_3^{2-}$, $MnO_4^-$, $HGaO_3^{2-}$, $HVO_4^{2-}$, $ClO_4^-$, $BO_3^{2-}$, pillaring anions such as $V_{10}O_{28}^{-6}$, and $MO_7O_{24}^{6-}$, monocarboxylates such as acetate, dicarboxylates such as oxalate, alkyl sulfonates such as laurylsulfonate as intercalating anions. Optionally, part of the anions are replaced with.

The Mg—Al anionic clay having $3R_2$ stacking may be prepared by hydrothermally treating a slurry containing an aluminum source and a magnesium source to form a Mg—Al anionic clay having $3R_2$ stacking.

Aluminum sources which are suitable for the preparation of the new polytype Mg—Al anionic clay are: crystalline aluminum trihydrate (ATH), for example gibbsites provided by Reynolds Aluminum Company RH-20® or JM Huber Micral® grades, BOC (Bauxite Ore Concentrate), bauxite, bayerite and nordstrandite, thermally treated forms of aluminum trihydrate, alumina sols, flash calcined alumina, gels, pseudo-boehmite, boehmite BOC and bauxite are the cheapest alumina sources which are excellently suitable starting material for the new polytype anionic clay. The alumina trihydrate is preferred to have a small particle size. Thermally treated forms of aluminum trihydrate are readily obtained by thermally treating aluminum trihydrate (gibbsite) at a temperature ranging from 100 to 800° C. for 15 minutes to 24 hours. In any event, the calcining temperature and time for obtaining calcined aluminum trihydrate should be sufficient to cause a measurable increase of the surface area in view of the surface area of the gibbsite as produced by the Bayer process which is generally between 30 and 50 $m^2/g$. It should be noted that within the concept of this invention flash calcined alumina is also considered to be a thermally treated form of aluminum trihydrate, although generally it is considered a totally different alumina. Flash calcined alumina is obtained by treating aluminum trihydrate at temperatures between 800–1000° C. for very short periods of time in special industrial equipment, as is described in U.S. Pat. Nos. 4,051,072 and 3,222,129. Combinations of various thermally treated forms of aluminum trihydrate can also be used. Also combinations of various alumina sources can be used. The aluminum source may be added as a solid, in suspension or in solution to the reactor to make the slurry. It may also be combined with the magnesium source prior to the addition to the reactor to form the slurry.

Magnesium sources which may be used include MgO and $Mg(OH)_2$, dolomite and sepiolite. Also combinations of Mg sources may be used. The magnesium source may be added to the reactor as a solid, a solution, or, preferably, as a slurry. The magnesium source may also be combined with the aluminum source before it is added the reactor to make a slurry.

As can be seen from the aluminum and magnesium sources mentioned above, it is possible to prepare the new polytype Mg—Al anionic clay from relatively inexpensive starting materials such as BOC and Gibbsite. Also for the magnesium source inexpensive material can be used such as inexpensive MgO grades. Especially when using these inexpensive magnesium sources, it is usually advisable to mill the magnesium source before use. Preferably, both the aluminum source and the magnesium source are milled before use to ensure reaction to the $3R_2$.anionic clay. When wet milling is used, the slurry containing both aluminum source and magnesium source may be wet milled, for instance in a ball mill, and directly transferred to the reactor which can operate under hydrothermal conditions.

An additional advantage of using inexpensive starting materials such as oxides and hydroxides, is the fact that no additional ions are introduced in to $3R_2$ Mg—Al anionic clay. This is also the case when using carbonates as starting materials. In that case, the process does not require washing of the product or filtering, there is no filtrate waste or gaseous emissions (e.g. from acid decomposition), making the process particularly environmental-friendly and more suited to the environmental constraints which are increasingly imposed on commercial operations. The product can be spray dried directly to form microspheres or can be extruded, palletized or beaded to form shaped bodies.

The new polytype Mg—Al anionic clay may also be shaped during preparation. In that case the $3R_2$ Mg—Al anionic clay is formed in shaped bodies by a process which comprises the steps of:

a) shaping the slurry of magnesium source and aluminum source into shaped bodies, b) optionally thermally treating the shaped bodies, and c) hydrothermally treating the shaped bodies to form anionic clay having $3R_2$ stacking in the shaped bodies.

In another embodiment $3R_1$-anionic clay containing shaped bodies are prepared by:

a) shaping a slurry of either an aluminum source and/or magnesium source into a shaped body, b) optionally treating the shaped body, and c) hydrothermally treating the shaped body in a solution containing aluminum source and/or magnesium source as to form anionic clay.

Suitable shaping methods include spray-drying, pelletising, extrusion (optionally combined with kneading), beading, or any other conventional shaping method used in the catalyst and absorbent fields or combinations thereof. The amount of liquid present in the slurry used for shaping should be adapted to the specific shaping step to be conducted. It might be advisable to (partially) remove the liquid used in the slurry and/or add additional or other liquid, and/or change the pH of the precursor mixture to make the slurry gellable and thus suitable for shaping. Various additives commonly used in the various shaping methods such as extrusion additives may be added to the precursor mixture used for shaping.

After shaping the shaped bodies may optionally be submitted to a thermal treatment. Such a treatment increases the physical strength of the particles. The thermal treatment can be conducted in an oxygen-containing atmosphere, in an inert atmosphere or in steam at temperatures varying from 30 to 1000° C. for a time ranging from a few minutes to 24 hours. As in, for instance, spray-drying a thermal treatment is inherently involved, a further thermal treatment may not be necessary.

Both with and without shaping prior to the formation of the $3R_2$ anionic clay the actual reaction to form the $3R_2Mg$—Al anionic clay is conducted under hydrothermal conditions. Within the context of this description this means in the presence of water (or steam) at a temperature above 100° C. at increased pressure. Preferably the reaction takes place in water in an autoclave at a temperature above 100° C., i.e. under autogeneous pressure.

If no shaping takes place before the hydrothermal treatment, the slurry containing aluminum source and magnesium source may simply be subjected to hydrothermal treatment. It is preferred to conduct the hydrothermal treatment in a "hydroxyl-rich" environment. This can be done by purging the slurry with nitrogen or inert gas or by adding hydroxyl anions to the hydrothermal treatment medium. For instance ammonium hydroxide may be added.

If the slurry is shaped first, and optionally thermally treated, the shaped bodies must be brought into contact with water or steam for the hydrothermal treatment.

If desired a preformed anionic clay may be added to the reaction mixture. Said preformed clay may be recycled anionic clay from the reaction mixture or anionic clay made separately by the process according to the invention.

Shaped bodies containing the new polytype Mg—Al anionic clay have not been described before, therefore the present invention is also directed to these shaped bodies containing $3R_2$ Mg—Al anionic clay.

Because of its simplicity, this process can be carried out in a continuous mode by mixing of a first slurry comprising aluminum source and a second slurry comprising magnesium source passing the mixed slurry, optionally after milling, through a reactor vessel which can operate under hydrothermal conditions. Said first and/or second slurry may be subjected to a treatment prior to mixing the slurries. The process may also be conducted in a continuous multi-step operation.

If desired inorganic acids and bases, for example for control of the pH, may be added to the slurry before or during reaction or to the individual reactants before combining them in the slurry. The acid and bases of choice are formic acid, acetic acid, nitric acid and ammonium hydroxide, because these types of acids and bases do not introduce unwanted ions in the reaction mixture.

If desired, the anionic clay prepared by the process according to the invention may be subjected to ion exchange. Upon ion exchange the interlayer charge-balancing anions are replaced with other anions. Upon ion exchange some of the anionic clay may be converted to a $3R_1$ stacking. Said other anions are the ones commonly present in anionic clays and include pillaring anions such as $V_{10}O_{28}^{-6}$, $Mo_7O_{24}^{6-}$. Said ion exchange can be conducted before drying or after the anionic clay is formed upon hydrothermal treatment.

The process of the invention provides wide flexibility in preparing products with a wide range of Mg:Al ratios. The Mg:Al ratio can vary from 0.1 to 10, preferably from 1 to 6, more preferred from 2 to 4, and especially preferred to close to 3.

For some applications it is desirable to have additives, both metals and non-metals, such as rare earth metals, Si, P, B, group VI, group VIII, alkaline earth (for instance Ca and Ba) and/or transition metals (for example Mn, Fe, Ti, Zr, Cu, Ni, Zn, Mo, Sn), or mixtures thereof present in or on the $3R_2$ Mg—Al anionic clay. Said metals can easily be deposited on the anionic clay. They can also be added either to the magnesium source or the aluminum source or to the slurry during preparation of the $3R_2$ Mg—Al anionic clay.

It is also possible to prepare a $3R_2$ type anionic clay by conversion of a $3R_1$ type anionic clay. To this end the $3R_1$ type anionic clay is calcined, rehydrated, and hydrothermally treated in a hydroxyl-rich environment. This can also be done with a $3R_1$ anionic clay containing shaped body. It is even possible to prepare a shaped body containing both $3R_1$ and $3R_2$ type anionic clay.

In another embodiment of the invention the $3R_2$ type is partly converted to a $3R_1$ type anionic clay. To this end the $3R_2$ type anionic clay is calcined, hydrated and hydrothermally treated in a carbonate-rich environment such as in the presence of $CO_2$ or by adding carbonate anions such as ammonium carbonate to the hydrothermal treatment medium.

It is also possible to prepare composites of both $3R_1$ and $3R_2$ type anionic clays. These composites may be prepared from a mixture of a Mg source which promotes $3R_2$ formation and a Mg source which promotes $3R_1$ formation and/or a Al source which promotes $3R_2$ formation and an Al source which promotes $3R_1$ formation. Mg sources which promote $3R_2$ type anionic clay formation have been described above. Mg sources which promote $3R_1$ type anionic clay formation are aluminum salts such as aluminum nitrate, aluminum chloride, aluminum chlorohydrate and sodium aluminate. Al sources which promote $3R_2$ type anionic clay formation have been described above. Al sources which promote $3R_1$ type anionic clay formation are magnesium salts such as magnesium acetate, magnesium formate, magnesium hydroxy acetate, hydromagnesite ($Mg_5(CO_3)_4(OH)_2$), magnesium carbonate, magnesium bicarbonate, magnesium nitrate, and magnesium chloride.

It should be noted that it is not necessary that all the Al source and all the Mg is converted into anionic clay. In some catalytic applications is is advantageous to have some unreacted (meaning: not reacted to anionic clay) Al-source and/or Mg source left in the product. For instance, in shaped bodies excess alumina improves the binding properties and both Mg and Al provide different types of desirable functionalities. For example, Al provides acid sites for catalytic cracking and improved nickel encapsulation and Mg provides basic sites which improve the suitability for removing or neutralizing strong acid streams of gasses or liquids.

The present invention is further directed to catalyst compositions comprising Mg—Al anionic clay having $3R_2$ stacking. Said catalyst composition may comprise all components usually present in catalyst compositions such as matrix and/or binder material, zeolites and additive components. The new polytype Mg—Al anionic clay may be incorporated into the catalyst composition as such or as shaped bodies. Said catalyst compositions may be used for hydrocarbon conversion reactions such catalytic cracking, hydrocracking, hydrogenation, polymerisation, steam reforming, base-catalysted reactions etcetera.

The new polytype Mg—Al anionic clay may also be combined with catalysts as additive compositions. Therefore, the present invention is also directed to catalyst additive compositions comprising Mg—Al anionic clay having $3R_2$ stacking. Said additive compositions usually comprise a matrix of binder material and optionally additional additive components. Again the new polytype Mg—Al anionic clay may be incorporated into the additive composition as such or as shaped bodies. Anionic clays are for instance known active components for $SO_x$ or $NO_x$ removal additive compositions in catalytic hydrocarbon conversion reactions. The $3R_2$ Mg—Al anionic clays according to the invention are also suitable active components for $SO_x$ or $NO_x$ removal additive compositions, especially when metals such as Ce and V are present in or on the anionic clay.

The $3R_2$ Mg—Al anionic clays according to the invention are further suitable for use as catalyst support, both when applied as such and applied as shaped bodies. For instance, the anionic clay may be used as support for Ziegler-Natta catalysts, for $CeO_2$ catalysts etctera.

The new polytype Mg—Al anionic clay can also be used in absorbent compositions and stabilizer compositions, both as such and as shaped bodies. For instance, the $3R_2$ Mg—Al anionic clay are excellent for use in stabilizer compositions for chlorine-containing (co)polymers, as halogen scavenger or as absorbent for waste water treatment or as flame retardant. Furthermore, the $3R_2$ Mg—Al anionic clay as a suitable active component in medicaments such as antiacids, antipeptin and stabilizer.

The present invention will be further illustrated by Examples which are not to be construed as limitative in any way.

EXAMPLES

Comparative Example 1

An Mg—Al hydrotalcite is prepared by thermally treating a slurry comprising gibbsite, flash calcined gibbsite and MgO at a temperature of 65° C. for 4 hours. The XRD pattern of the product shows that a Mg—Al anionic clay is formed having $3R_1$ stacking.

Example 2

An Mg—Al hydrotalcite is prepared by hydrothermally treating a slurry comprising gibbsite, flash calcined gibbsite and milled MgO at a temperature of 180° C. for 1 hour. The XRD pattern of the product shows that a Mg—Al anionic clay is formed having $3R_2$ stacking.

Example 3

In a 10 liter autoclave MgO (ex Merck®) and BOC in a ratio 4:1 were slurried. The slurry was milled and hydrothermally treated at 170° C. for 90 minutes. The XRD pattern of the product showed the presence of $3R_2$ type anionic clay.

Example 4

In a 10 liter autoclave MgO (ex Nedmag®) and BOC in a ration 4:1 were slurried. The slurry was milled and hydrothermally treated at 170° C. for 90 minutes. The XRD pattern of the product showed the presence of $3R_2$ type anionic clay.

What is claimed is:

1. Mg—Al anionic clay having interlayer spacing with a hydroxyl group anion contained in the interlayer spacing, said clay having $3R_2$ stacking.

2. The Mg—Al anionic clay of claim 1 wherein the interlayer spacing contains in addition to the hydroxyl anion, at least one intercalating anion selected from the group consisting of $NO_3^-$, $OH^-$, $Cl^-$, $Br^-$, $I^-$, $CO_3^{2-}$, $SiO_3^{2-}$, $SO_4^{2-}$, $CrO_4^{2-}$, $BO_3^{2-}$, $MnO_4^-$, $HGaO_3^{2-}$, $HVO_4^{2-}$, $ClO_4^-$, $BO_3^{2-}$, pillaring anions, monocarboxylates, dicarboxylates, and alkyl sulfonates.

3. The Mg—Al anionic clay of claim 1 wherein additives are present in the anionic clay.

4. The Mg—Al anionic clay of claim 3 wherein the additives are selected from the group consisting of rare earth metals, Si, P, B, group VI metals, Group VIII metals, alkaline earth metals, transition metals, and mixtures thereof.

5. The Mg—Al anionic clay of claim 4 wherein the alkaline earth metals are selected from the group consisting of Ca and Ba.

6. A process for the preparation of an Mg—Al anionic clay having $3R_2$ stacking wherein a slurry containing an aluminum source and a magnesium source is hydrothermally treated to form a Mg—Al anionic clay having $3R_2$ stacking.

7. The process of claim 6, wherein the magnesium source is milled prior to the hydrothermal treatment of the slurry.

8. The process of claim 7, wherein the magnesium source is milled prior to its addition to the slurry..

9. The process of claim 6 wherein the magnesium source and aluminum source are milled prior to the hydrothermal treatment.

10. The process of claim 6 comprising the steps of:
    a) shaping the slurry of magnesium source and aluminum source into shaped bodies,
    b) optionally thermally treating the shaped bodies, and
    c) hydrothermally treating the shaped bodies to form anionic clay having $3R_2$ stacking in the shaped bodies.

11. A process for the preparation of Mg—Al anionic clay having $3R_2$ stacking wherein an anionic clay having $3R_1$ stacking is calcined, rehydrated and thermally treated to form Mg—Al anionic clay with $3R_2$ stacking.

12. Shaped bodies containing Mg—Al anionic clay with hydroxide anions in its interlayer spacing having $3R_2$ stacking.

13. A catalyst composition comprising Mg—Al anionic clay with hydroxide anions in its interlayer spacing having $3R_2$ stacking.

14. A catalyst composition comprising shaped bodies which contain Mg—Al anionic clay with hydroxide anions in its interlayer spacing having $3R_2$ stacking.

15. A catalyst additive composition comprising Mg—Al anionic clay with hydroxide anions in its interlayer spacing having $3R_2$ stacking.

16. A process for the removal of SOx or NOx in a catalytic hydrocarbon conversion reaction by having the catalyst additive composition of claim 15 present in said reaction.

17. A catalyst additive composition comprising shaped bodies which contain Mg—Al anionic clay with hydroxide anions in its interlayer spacing having $3R_2$ stacking.

18. A catalyst support comprising Mg—Al anionic clay with hydroxide anions in its interlayer spacing having $3R_2$ stacking.

19. A catalyst support comprising shaped bodies which contain Mg—Al anionic clay with hydroxide anions in its interlayer spacing having $3R_2$ stacking.

20. An absorbent composition comprising Mg—Al anionic clay with hydroxide anions in its interlayer spacing having $3R_2$ stacking.

21. An absorbent composition comprising shaped bodies which contain Mg—Al anionic clay with hydroxide anions in its interlayer spacing having $3R_2$ stacking.

22. A stabilizer composition comprising Mg—Al anionic clay with hydroxide anions in its interlayer spacing having $3R_2$ stacking.

23. A method for stabilizing chlorine-containing co-polymers comprising combining the composition of claim 22 with said co-polymers.

24. A stabilizer composition comprising shaped bodies which contain Mg—Al anionic clay with hydroxide anions in its interlayer spacing having $3R_2$ stacking.

25. A medicament comprising Mg—Al anionic clay with hydroxide anions in its interlayer spacing having $3R_2$ stacking.

* * * * *